United States Patent

Dabi et al.

Patent Number: 5,624,421
Date of Patent: Apr. 29, 1997

[54] ABSORBENT PRODUCTS HAVING FLEXIBLE HYDROPHILIC WICK MEANS

[75] Inventors: Shmuel Dabi, Highland Park; Kenneth Kraskin, Milltown, both of N.J.

[73] Assignee: McNeill-PPC, Inc., Skillman, N.J.

[21] Appl. No.: 621,702

[22] Filed: Mar. 26, 1996

Related U.S. Application Data

[63] Continuation of Ser. No. 334,449, Nov. 4, 1994, abandoned, which is a continuation of Ser. No. 24,879, Mar. 1, 1993, abandoned, which is a continuation of Ser. No. 777,427, Oct. 11, 1991, abandoned, which is a continuation of Ser. No. 649,281, Jan. 30, 1990, abandoned, which is a continuation of Ser. No. 431,059, Nov. 3, 1989, abandoned.

[51] Int. Cl.$^6$ .................. A61F 13/15; A61F 13/20
[52] U.S. Cl. .................. 604/378; 604/358; 604/385.1
[58] Field of Search .................. 604/358, 369, 604/378, 379, 380, 385.1, 385.2, 387, 904

[56] References Cited

U.S. PATENT DOCUMENTS

| | | | |
|---|---|---|---|
| Re. 24,137 | 4/1956 | Jacks | 604/378 |
| 2,092,346 | 9/1937 | Arone | 604/904 |
| 3,183,909 | 5/1965 | Roehr | 604/377 |
| 3,420,234 | 1/1969 | Phelps | 604/904 |
| 4,029,100 | 6/1977 | Karami | 604/368 |
| 4,046,147 | 9/1977 | Berg | 604/385.1 |
| 4,425,130 | 1/1984 | Des Marais | 604/389 |
| 4,433,972 | 2/1984 | Malfitano | 604/385.1 |
| 4,559,051 | 12/1985 | Hanson | 604/385.1 |
| 4,605,405 | 8/1986 | Lassen | 604/390 |
| 4,623,341 | 11/1986 | Roeder | 604/378 |
| 4,631,062 | 12/1986 | Lassen et al. | 604/378 |
| 4,673,403 | 6/1987 | Lassen et al. | 604/361 |
| 4,753,644 | 6/1988 | Cottenden et al. | 604/378 |
| 4,778,459 | 10/1988 | Fuisz | 604/385.1 |
| 4,816,025 | 3/1989 | Foreman | 604/378 |
| 4,988,345 | 1/1991 | Reising | 604/378 |
| 5,007,906 | 4/1991 | Osborn, III et al. | 604/385.1 |

FOREIGN PATENT DOCUMENTS

2042343  9/1980  United Kingdom .................. 604/378

*Primary Examiner*—V. Millin
*Assistant Examiner*—Ronald K. Straight, Jr.
*Attorney, Agent, or Firm*—James P. Barr

[57] ABSTRACT

Sanitary napkins and other absorbent products as well as a method for their use are provided by this invention. The sanitary napkin includes wick structure disposed on a body-facing side of the napkin which is biased away from the body-facing side to provide a body-contacting portion disposed in a different plane from the plane of the body-facing side.

18 Claims, 3 Drawing Sheets

ABSORBENT PRODUCTS HAVING FLEXIBLE HYDROPHILIC WICK MEANS

This is a continuation of application Ser. No. 08/334,449 filed Nov. 4, 1994, now abandoned, which is a continuation of Ser. No. 08/024,879, filed Mar. 1, 1993, now abandoned, which is a continuation of Ser. No. 07/771,427 filed Oct. 11, 1991, now abandoned, which is a continuation of Ser. No. 07/649,281, filed Jan. 30, 1990, now abandoned, which is a continuation of Ser. No. 07/431,059, filed Nov. 3, 1989, now abandoned.

FIELD OF THE INVENTION

This invention relates to protective, absorbent products, such as sanitary napkins and pads, which provide better contact with the body for more adequate protection than those currently available.

BACKGROUND OF INVENTION

In the past, sanitary napkins have been constructed using an absorbent element having a body-facing side for receiving body fluids and an undergarment-facing side which may be lined or treated to render it impervious to body fluids. Although these sanitary napkins have sufficient absorbent capacity to collect and contain menstrual discharge, they often fall short in protecting against leakage at their sides and ends. Such failure may be due to the lack of continuous contact between the perineal area and the absorbent pad. For example, sanitary napkins designed to be attached adhesively to an undergarment tend to shift and move in tandem with the undergarment in response to the wearer's activity. Also, the absorbent cores of these sanitary napkins are often made of wood pulp fluff, which permanently deforms under relatively light compressive loads. Consequently, during use, a space usually forms between the napkin and the perineal area of the user, causing viscous fluid to flow along the body and stain the back part of the undergarment without being absorbed by the pad.

Several artisans have attempted to provide better body contact by providing a raised center or profile on the body-facing side of the napkin. See Lassen et al., U.S. Pat. No. 4,673,403 ('403), Jun. 16, 1987; Lassen et al., U.S. Pat. No. 4,631,062 ('062), Dec. 23, 1986; Roeder, U.S. Pat. No. 4,623,341 ('341), Nov. 18, 1986; Lassen et al., U.S. Pat. No. 4,605,405 ('405), Aug. 12, 1986; DesMarais, U.S. Pat. No. 4,425,130, Jan. 10, 1984; Roehr, U.S. Pat. No. 3,183,909 ('909), May 18, 1965; and Jacks, U.S. Pat. No. 2,662,527, Dec. 15, 1953, which are hereby incorporated by reference.

Lassen '403 discloses an incontinent garment or feminine pad having a indicator thereon to aid in the proper placement of the pad onto the body of a wearer. The pad includes a raised profile for locating the pad with respect to fluid flow within the vestibule of the wearer.

Lassen '062 describes a labial pad having an anatomically comfortable configuration including a laterally upwardly directed projection flowing generally along the longitudal axis within the posterior region of the pad and a prominence near the distal end which extends toward and tapers to the proximal end.

Roeder '341 describes a combination sanitary napkin and interlabial pad which includes an absorbent layer which tapers at one end and which is designed to fold over onto itself to form a double layer with the top layer designed, due to its reduced width, to engage the labia of the user. The upper layer of the pad is moveable with respect to the bottom absorbent layer.

Lassen '405 discloses a sanitary napkin which is provided with a positioning strap in slidable contact with a low friction baffle which is attached to the bottom of the napkin. The contact between the positioning strap and the baffle is maintained by a retention strap attached to the napkin which encircles the positioning strap. The napkin is dynamically moveable during use.

DesMarais, discloses a compound sanitary napkin including a primary menstrual pad and a panty protector joined at their respective transverse ends. The two members are free to move relative to one another along essentially the entire common length.

Roehr '909 discloses a convertible sanitary napkin which can alternatively provide a traditional menstrual pad and a semi-internally worn variation.

Jacks, discloses a sanitary pad having a raised center portion for positioning within a women's vestibule.

While these products provide a better anatomical fit, there remains a need for a slimmer and more comfortable sanitary napkin capable of maintaining good body contact without sacrificing the convenience of attachment to the undergarment. There is also a need for a napkin design which substantially prevents both early failures and "body" failures attributed to poor fit without sacrificing comfort.

SUMMARY OF THE INVENTION

This invention relates to sanitary napkins, and other products, which contain an absorbent element having a body-facing side, an undergarment-facing side and wick means for absorbing body fluid disposed on the body-facing side. The wick means is biased away from the body-facing side to provide a body-contacting portion disposed in a different plane from that of the plane of the body-facing side. Although this invention is well-suited for use in sanitary napkins, it may be used equally well in adult and infant diapers, incontinence pads and the like. The products of this invention aid in decreasing the likelihood that body fluid will soil the undergarment of the user by collecting the body fluid in the wick means and then preferentially drawing the body fluid into the absorbent element.

Preferably, the wick means of this invention is composed of a soft, flexible, resilient hydrophilic material, which maintains good body contact regardless of the deformation and movement of the absorbent element. The soft contact of the fluid transfer wicks of this invention result in greater protection without the bulkiness and discomfort associated with large absorbent inserts.

The wick means of the products of this invention are preferably attached to the body-facing side of the napkin, or other absorbent product, at at least two spaced apart anchoring locations and are disposed to curve over the body-facing side of the product to provide a body-contacting portion at a position intermediate of the anchoring locations. Since it is preferable that the absorbent element draw body fluid from the wick, the absorbent element should comprise a greater capillary pressure than the wick.

It is, therefore, an object of this invention to provide a sanitary napkin capable of maintaining good body contact without sacrificing comfort and the convenience of attachment to an undergarment.

It is another object of this invention to provide absorbent products which are more leakproof and adaptable to the user's activity.

With these and other objects in view, this invention resides in the novel construction, combination, arrangement of parts, and methods substantially as hereinafter described and more particularly defined in the attached claims.

BRIEF DESCRIPTION OF THE DRAWINGS

The accompanying drawings illustrate preferred embodiments of the invention according to the practical application of the principles thereof, and in which.

DESCRIPTION OF THE INVENTION

The preferred operable embodiments of this invention will now be described. In one embodiment, a sanitary napkin is provided with an absorbent element having longitudinally extending sides, transverse ends, a body-facing side and an undergarment-facing side. The napkin further includes wick means for absorbing body fluid attached to said body-facing side. The wick means is biased (i.e.; supported, predisposed, or urged) away from the body-facing side to provide a body-contacting portion disposed in a plane spaced apart from the plane of said body-facing side.

This napkin can be employed in a preferred method of collecting body fluids in which the described napkin is applied to an inner crotch area of an undergarment, so as to enable the collection of body fluid in the wick means. The absorbed body fluid in the wick is then transferred to the absorbent element so as to decrease the likelihood that body fluid will soil the undergarment.

Figure 1:
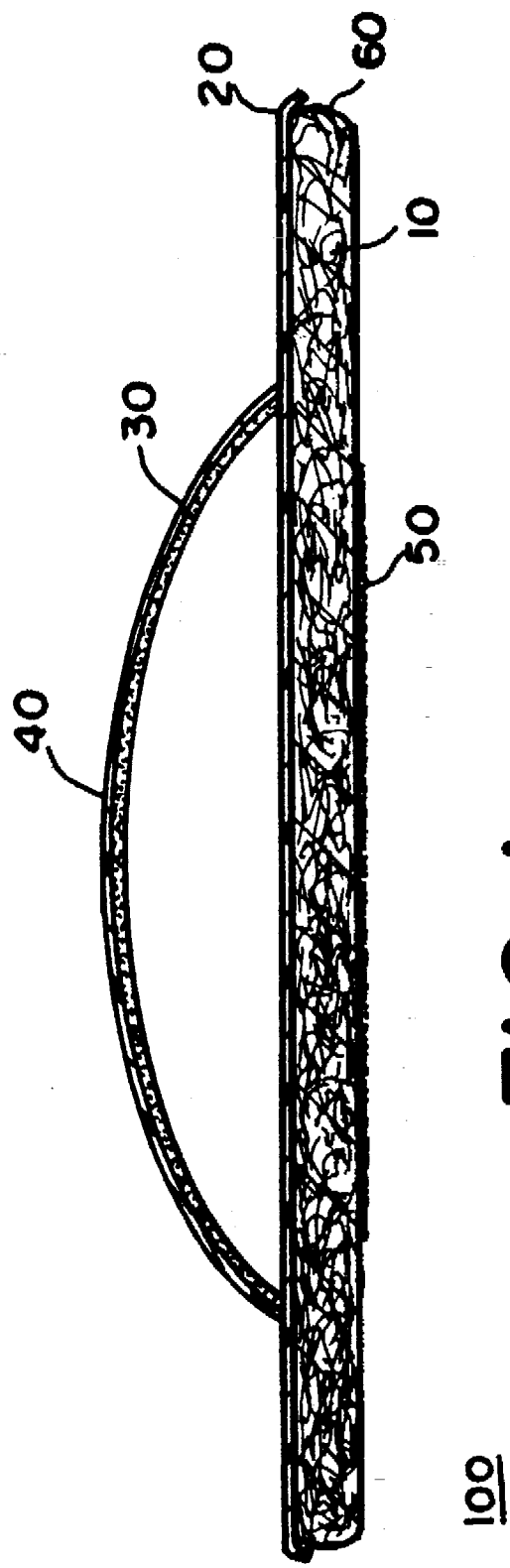
FIG. 1 is a side view of a preferred sanitary napkin of this invention illustrating its construction.
Figure 2:
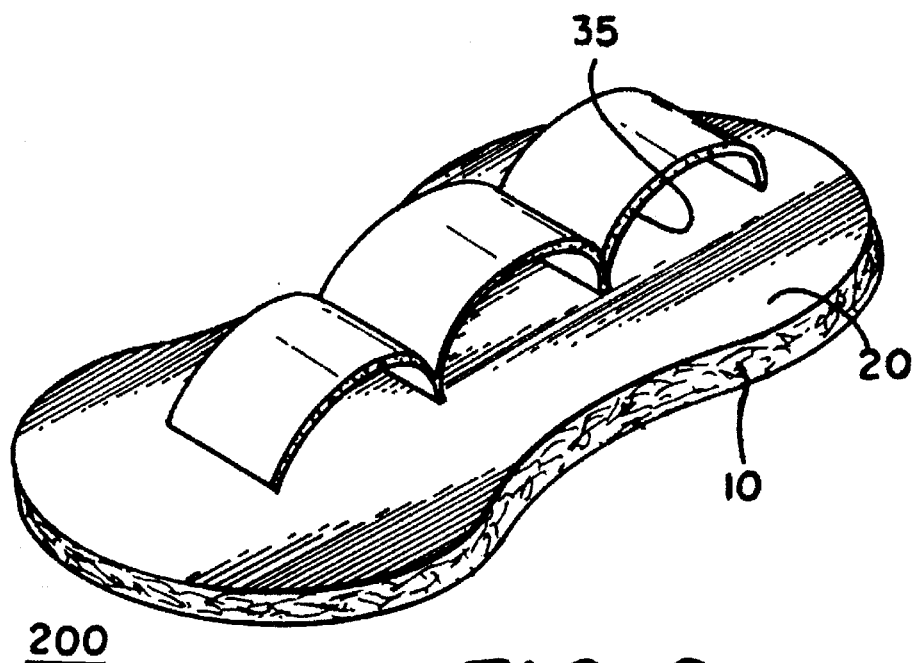
FIG. 2 is a perspective view of an alternative napkin embodiment describing at least three spaced apart anchoring locations for a preferred wick design.

With reference to the Figures, and particularly to FIG. 1 thereof, there is provided a sanitary napkin 100 having a wick 30 or 35, preferably made from absorbent and resilient material which is curved in the shape of an arch. Alternatively, the wick can be curved in a plurality of arches, as substantially described by embodiment 200 in FIG. 2. The wick 30 or 35 of this invention should be able to absorb body fluids, but also should readily transfer these fluids to the absorbent element 10. Suitable materials for the wick are resilient foams or fibrous structures, which form low contact angles with fluids, and are readily wettable. Preferably these materials include relatively large pores, so as to minimize the wick's ability to retain the absorbed fluids, and permit facilitated delivery of these fluids to the absorbent element 10. Acceptable materials for the wick 30 or 35 are hydrophilic resilient foams such as polyaminoether foam. See U.S. Pat. No. 4,554,297, which is hereby incorporated by reference. Other hydrophilic foams can also be favorably employed, such as polyurethane (Hypol®) available from W. R. Grace. In addition to being absorbent and preferably nonretentive, the wick should be soft and resilient enough to maintain the arch shape when no pressure is applied to it. Preferably, the wick 30 or 35 is disposed to vault away from the body-facing side to provide one or more body-contacting portions at positions intermediate to its anchoring locations. Thus, even when the absorbent element 10 is not held close to the body of the wearer, the resilient arch will maintain the contact to assure fluid uptake and thus reduce the possibility of failure.

The absorbent element 10 of this invention preferably is made from a more aggressive absorbent material than the wick 30 or 35. In other words, the absorbent element 10 preferably comprises a greater capillary pressure than the wick so that a fluid deposited on the wick will be readily transferred into the absorbent element 10 and will be retained there after equilibrium is attained. Greater capillary pressure can be achieved by the selection of materials or treatments which provide a low contact angle between the fluid and the capillary wall, or by providing a smaller pore size or greater density. The absorbent element 10 can contain conventional resilient material for enabling the napkin 100 to bend easily without excessive distortion. Such materials include compacted cellulosic fibers and hydrocolloidal material such as those described by Kopolow, U.S. Pat. No. 4,550,142, which is herein incorporated by reference. The preferred absorbent element 10 can be approximately 4 to 12 inches long, preferably about 10 to 11 inches. It generally comprises a core, which preferably is made of loosely associated absorbent hydrophilic materials such as cellulosic fibers, wood pulp, fluff, sphagnum moss, super-absorbents, regenerated cellulose, or cotton fibers, and/or other materials generally known in the art. The absorbent element 10 may be either rectangular or shaped, and may even include side protecting flaps.

The body-facing side of the absorbent element 10 preferably may contain a body fluid pervious surface 20. The body fluid pervious surface 20 can be made of any relatively nonabsorbent, fluid pervious material. This material is provided for comfort and conformability and directs fluid to an underlying layer, for example, wood pulp, which retains such fluids. This surface may be a woven, or nonwoven material pervious to body fluid. Furthermore, it should retain little or no fluid in its structure so as to provide a relatively dry surface next to the skin. Generally, the body fluid pervious surface 20 is a single, rectangular sheet of material having a width sufficient to cover the body-facing side of the absorbent element 10. Preferably, the body fluid pervious surface 20 is longer than the core so as to form end tabs, which may be sealed with other pervious or nonpervious layers of the absorbent element 10 to fully enclose the core. The body fluid pervious surface 20 is preferably made of fibers or filaments of thermoplastic polymers such as polyethylene or polypropylene or apertured polymeric film.

For aesthetic reasons, the wicks described herein can alternatively be disposed beneath the body fluid pervious surface 20 which, in turn, can be more loosely sealed with the other pervious or nonpervious layers to fully enclose the core. It is understood that the benefits achieved by biasing a flexible hydrophilic wick beneath the body fluid pervious surface 20 of the absorbent element would be similar to those obtained by wicks disposed above the body fluid pervious surface 20, previously described. It is further understood that these wicks could be affixed or preformed in an arch shape and merely rested on the core, as opposed to being attached to the core, prior to sealing the body fluid pervious surface 20.

The preferred wick means of this invention can also include a body fluid pervious sheet 40 disposed on its body-facing side, as described in FIG. 1. This body fluid pervious sheet 40 is preferably heat sealed to the convex side of the flexible hydrophilic foams which make up the preferred wicks. The body fluid pervious sheet 40 can also be adhesively attached to the wicks.

Figure 3:
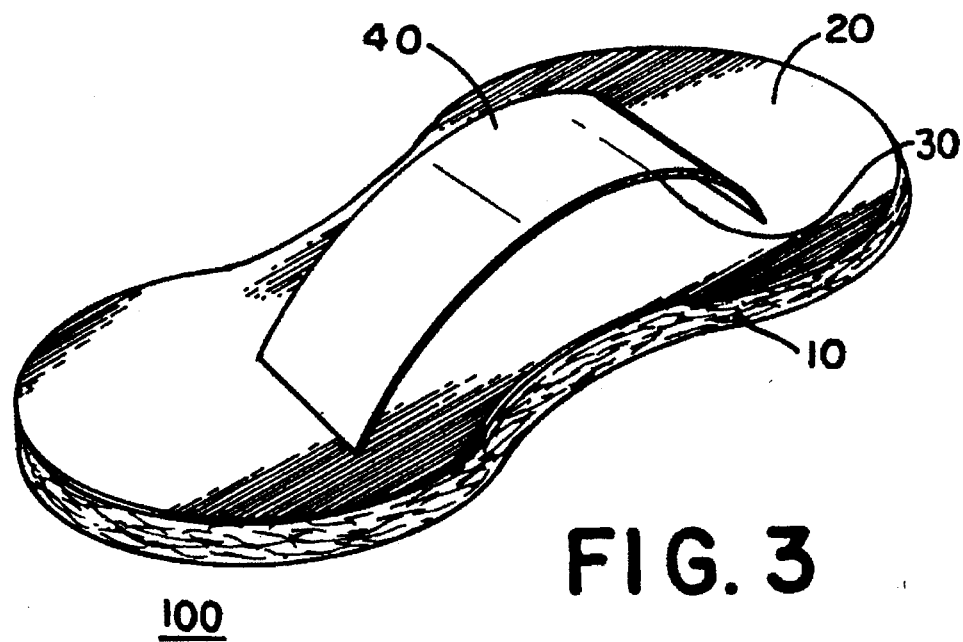
FIG. 3 is a perspective view of the sanitary napkin of FIG. 1 illustrating a wick attached to the body-facing side at two spaced apart anchoring locations.
Figure 5:
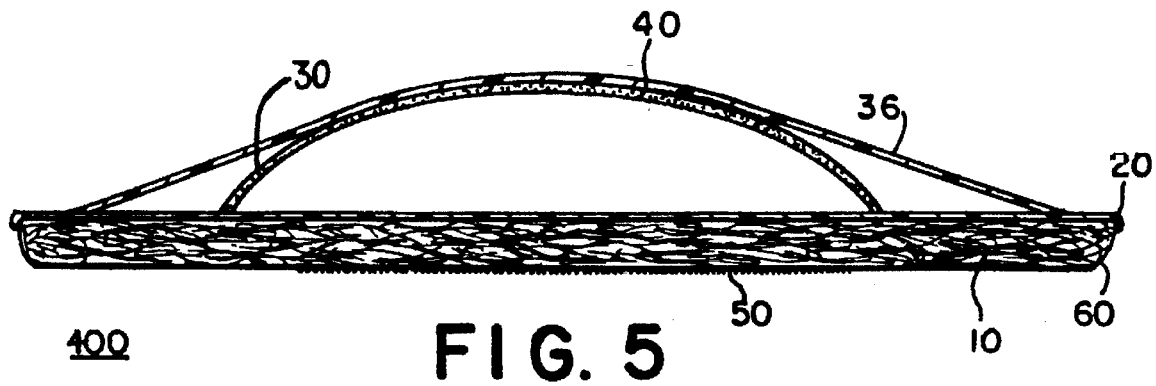
FIG. 5 is a cross-sectional side view of the napkin embodiment of FIG. 4.
Figure 4:
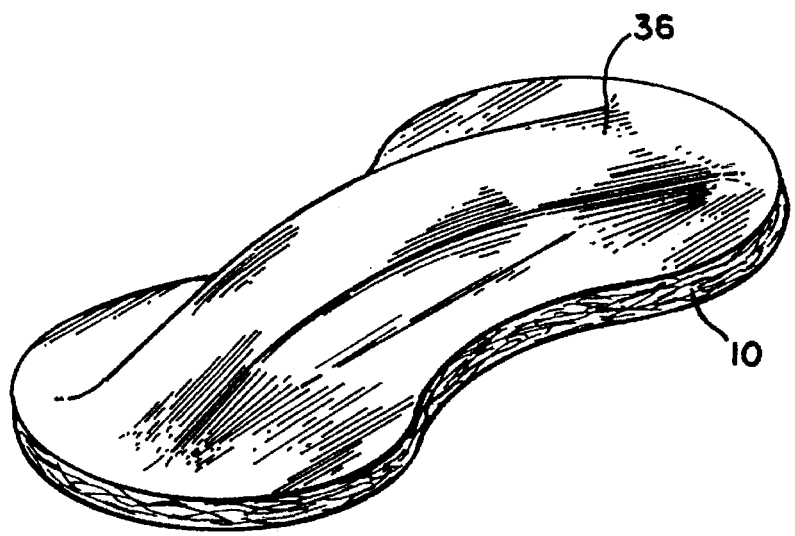
FIG. 4 is a perspective view of another napkin embodiment wherein the wick is disposed beneath a body fluid pervious cover.

Referring to FIGS. 4 and 5, another embodiment 400 of this invention is described. A body fluid pervious cover 36 is disposed over the wick 30 as substantially described in FIG. 3, and attached to the body-facing side of the absorbent element 10. The body fluid pervious cover 36 preferably entraps the wick 30 beneath a visually appealing surface. The body fluid pervious cover 36 is preferably attached, via heat sealing or adhesive, to the body fluid pervious surface 20 of the absorbent element 10 and should provide sufficient room for the preferred arches of the wick 30 to vault away from the absorbent element 10.

Underlying the core of the absorbent element 10 can be another layer of absorbent material (not shown) to provide additional resiliency to the product. This absorbent layer can extend beyond the longitudinal sides of the absorbent core to entrap any body fluid which escapes from the sides of the absorbent element 10. This layer may also be substantially wider than the core of the absorbent element and may extend into the flaps. The absorbent layer may comprise a thin, absorbent sheet of material such as tissue, fabric, or the like, made of cellulosic fibers. Because such material is provided as a safety measure and is only required to contain escaped fluid, it need not be very absorbent at all, and, in fact, may be comprised of any capillary or cellular system including hydrophobic material. However, the preferred material is a hydrophilic fabric comprised of cellulosic fibers, such as wood pulp tissue or other suitable hydrophilic woven or nonwoven material. The preferred absorbent layer has the advantage of providing resiliency and conformability to the product.

The sanitary napkin 100 of this invention further preferably includes a body fluid impervious surface 60 on its undergarment-facing side. The preferred body fluid impervious surface 60 will permit the passage of air and moisture vapor while blocking the passage of fluid to the outer surface of the napkin. The body fluid impervious surface 60 may be heat sealed or fastened by way of adhesives to a core or to a core wrapped in a pervious surface cover. Such impervious surfaces may comprise any thin, flexible, body fluid impermeable material such as a polymeric film, for example, polyethylene, polypropylene, cellophane or even a normally fluid pervious material that has been treated to be impervious, such as impregnated fluid repellent paper or nonwoven fabric material. In the most preferred embodiments of this invention, the body fluid impervious surface 60 includes a plastic film of polyethylene or a bicomponent film such as an EVA/PE coextruded film.

Also included with this invention is an attachment adhesive element 50 which can be made of any known, pressure-sensitive adhesive material. As used herein, the term "pressure-sensitive" refers to any releasable adhesive or releasable tenacious means. Adhesive compositions suitable for sanitary napkins, include, for example, a water-based, pressure-sensitive adhesive such as an acrylate adhesive. Alternatively, the adhesive may comprise a rapid setting thermoplastic "hot-melt", rubber adhesive, or two-sided adhesive tape. As is customary in the art, a preferred kraft paper release strip can also be applied to the adhesive element 50 to protect it before use.

From the foregoing, it can be realized that this invention provides sanitary napkins and other products which obtain the benefit of good body contact without sacrificing comfort or convenient attachment mechanisms. Although various embodiments have been illustrated, this was for the purpose of describing, but not limiting the invention. Various modifications, which will become apparent to one skilled in the art, are within the scope of this invention described in the attached claims.

We claim:

1. A sanitary napkin comprising:
   (a) an absorbent element having longitudinally extending sides, transverse ends, a body-facing side and an undergarment-facing side; and
   (b) resilient wick means disposed on said body-facing side, said wick means having means for absorbing body fluid and thereafter transporting said body fluid to said absorbent element, said wick means being anchored to said absorbent element at at least two spaced apart anchoring locations interior of the transverse ends such that said wick means is arched and biased away from said body-facing side to provide a body-contacting portion intermediate of the anchoring locations, said wick means being supported in said arched shape by its resiliency and unsupported by any structure except the inherent support supplied by the resiliency of the wick means, wherein said body fluid is first drawn into said wick means and then into said absorbent element and, wherein said wick means has an absorbency less than the absorbency of said absorbent element.

2. The sanitary napkin of claim 1 wherein said wick means comprises resilient absorbent material.

3. The sanitary napkin of claim 2 wherein said body-facing side of said absorbent element comprises a body fluid pervious surface.

4. The sanitary napkin of claim 3 wherein said wick means is disposed on said body fluid pervious surface of said absorbent element.

5. The sanitary napkin of claim 2 wherein said wick means comprises a hydrophilic foam material.

6. The sanitary napkin of claim 2 further comprising a body fluid pervious sheet attached to a body-facing side of said wick means.

7. The sanitary napkin of claim 2 further comprising a body fluid pervious cover disposed over said wick means and attached to said absorbent element so as to substantially entrap said wick means thereunder.

8. The sanitary napkin of claim 1 wherein said absorbent element comprises a greater capillary pressure than said wick means.

9. The sanitary napkin of claim 1 wherein said wick means comprises a fibrous structure.

10. The sanitary napkin of claim 1 wherein said absorbent element comprises one or more of wood pulp, sphagnum moss, and super-absorbent.

11. The sanitary napkin of claim 1 wherein said absorbent element is the primary absorbent for said sanitary napkin.

12. A sanitary napkin comprising;
   (a) an absorbent element having longitudinally extending sides, transverse ends, a body-facing side and an undergarment-facing side;
   (b) a resilient wick for absorbing body fluid and for transporting said body fluid to said absorbent element, said wick means disposed on said body-facing side, said wick being anchored to said absorbent element at at least two spaced apart anchoring locations interior of the transverse ends such that said wick is arched and biased away from said body-facing side to provide a body-contacting portion intermediate of the anchoring locations, said wick being supported in said arched shape only by its resiliency, and unsupported by any structure except the inherent support supplied by the resiliency of the wick, wherein said body fluid is first drawn into said wick and then into said absorbent element; and
   (c) a body fluid pervious cover disposed over said wick and attached to said absorbent element so as to substantially entrap said wick thereunder; said absorbent element having a greater capillary pressure than said wick so as to draw body fluid therefrom and, wherein said wick has an absorbency less than the absorbency of said absorbent element.

13. The sanitary napkin of claim 12 wherein said resilient wick comprises hydrophilic foam.

14. The sanitary napkin of claim 12 wherein said resilient wick comprises resilient means for permitting said wick to maintain substantial perineal contact when said absorbent element shifts from close contact with the perineal area of the wearer during use.

15. An absorbent product comprising:
   (a) an absorbent element having longitudinally extending sides, transverse ends, a body-facing side and an undergarment-facing side; and
   (b) resilient wick means for absorbing body fluid attached to said body-facing side of the absorbent element, said wick means being anchored to said absorbent element at at least two spaced apart anchoring locations such that said wick means is arched and biased away from said body-facing side to provide a body-contacting portion intermediate of the anchoring locations, said wick means being supported in said arched shape only by its resiliency, and unsupported by any structure except the inherent support supplied by the resiliency of the wick means, wherein said body fluid is first drawn into said wick means and then into said absorbent element and, wherein said wick means has an absorbency less than the absorbency of said absorbent element.

16. An absorbent article for use on the body of a user, comprising:
   (a) A primary absorbent element having a body-facing side and an undergarment-facing side; and
   (b) resilient wick disposed on said body-facing side for absorbing body fluid and thereafter transporting at least a portion of said body fluid absorbed to said primary absorbent element, said wick being formed into an arcuate shape adapted to resiliently bias said wick against said user's body, said wick having sufficient resiliency to maintain said arcuate shape when no pressure from said user's body is applied to said wick, and unsupported by any structure except the inherent support supplied by the resiliency of the wick and wherein said body fluid is first drawn from said wick and then into said absorbent element and, wherein said wick has an absorbency less than the absorbency of said absorbent element.

17. A sanitary napkin comprising:
   (a) an absorbent element having longitudinally extending sides, transverse ends, a body-facing side and an undergarment-facing side; and
   (b) resilient wick means disposed on said body-facing side, said wick means having means for absorbing body fluid and thereafter transporting said body fluid to said absorbent element, said wick means being anchored to said body-facing side of said absorbent element at at least three spaced apart anchoring locations interior of the transverse ends such that said wick means is arched and biased away from said body-facing side to provide a plurality of body-contacting portions intermediate of the anchoring locations, said wick means being supported in said arched shape only by its resiliency, and unsupported by any structure except the inherent support supplied by the resiliency of the wick means, wherein said body fluid is first drawn into said wick means and then into said absorbent element and, wherein said wick means has an absorbency less than the absorbency of said absorbent element.

18. A method of collecting body fluids, comprising the steps of:
   (a) providing a sanitary napkin having an absorbent element having longitudinally extending sides, transverse ends, a body-facing side, and undergarment-facing side and resilient wick means for absorbing body fluid and thereafter transporting said body fluid to said absorbent element wherein said wick means has an absorbency less than the absorbency of said absorbent element, said wick means attached to said body-facing side and anchored at at least two spaced apart anchoring locations to said absorbent element and is disposed interior of the transverse ends such that said wick means is arched and biased away from said body-facing side to provide a body-contacting portion intermediate of the anchoring locations, said wick means being supported in said arched shape only by its resiliency, and unsupported by any structure except the inherent support supplied by the resiliency of the wick means, wherein said body fluid is first drawn into said wick means and then into said absorbent element;
   (b) applying the garment-facing side of said napkin to an inner crotch area of an undergarment;
   (c) collecting said body fluid in said wick means; and
   (d) drawing body fluid collected by the wick means into said absorbent element to thereby decrease the likelihood that body fluid will soil said undergarment.

* * * * *